United States Patent
Sugawara et al.

(10) Patent No.: US 10,639,243 B2
(45) Date of Patent: May 5, 2020

(54) DENTAL PRIMER AND KIT FOR DENTAL PROSTHESIS ADHESION

(71) Applicant: GC Corporation, Shizuoka (JP)

(72) Inventors: Ayaka Sugawara, Tokyo (JP); Naofumi Matsumoto, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 15/920,913

(22) Filed: Mar. 14, 2018

(65) Prior Publication Data

US 2018/0280251 A1  Oct. 4, 2018

(30) Foreign Application Priority Data

Mar. 30, 2017 (JP) ................................. 2017-067025

(51) Int. Cl.

| | | |
|---|---|---|
| *C08F 2/46* | (2006.01) | |
| *C08F 2/50* | (2006.01) | |
| *C08G 61/04* | (2006.01) | |
| *A61K 6/30* | (2020.01) | |
| *A61K 6/40* | (2020.01) | |

(52) U.S. Cl.
CPC . *A61K 6/30* (2020.01); *A61K 6/40* (2020.01)

(58) Field of Classification Search
CPC ..... A61K 6/0023; A61K 6/0029; C08L 33/08; C08L 33/10; C08L 33/06; C08L 43/02
USPC ................. 522/66, 6, 71, 1, 189, 184; 520/1
See application file for complete search history.

(56) References Cited

U.S. PATENT DOCUMENTS

| | | | | |
|---|---|---|---|---|
| 4,731,146 A | * | 3/1988 | Clark | .......................... C09J 4/00 156/314 |
| 4,990,281 A | * | 2/1991 | Clark | .......................... C09J 4/00 252/183.13 |
| 5,290,172 A | * | 3/1994 | Sakuma | ............... A61K 6/0023 106/35 |
| 5,866,631 A | * | 2/1999 | Nakagawa | ........... A61K 6/0052 522/29 |
| 2009/0305194 A1 | * | 12/2009 | Rusin | .................. A61K 6/0017 433/217.1 |
| 2010/0216096 A1 | * | 8/2010 | Suzuki | ................... A61K 6/083 433/217.1 |
| 2010/0304961 A1 | * | 12/2010 | Kimura | ................ A61K 6/0023 502/160 |
| 2010/0311864 A1 | * | 12/2010 | Arita | .................... A61K 6/0029 523/118 |
| 2013/0012615 A1 | * | 1/2013 | Hinamoto | ............ A61K 6/0023 523/116 |
| 2016/0051450 A1 | | 2/2016 | Kashiki et al. | |
| 2017/0135909 A1 | * | 5/2017 | Takei | ....................... A61K 6/00 |
| 2017/0196778 A1 | * | 7/2017 | Nojiri | ...................... A61K 6/00 |

FOREIGN PATENT DOCUMENTS

JP   2010-280630   12/2010

\* cited by examiner

*Primary Examiner* — Jessica Whiteley
(74) *Attorney, Agent, or Firm* — IPUSA, PLLC

(57) ABSTRACT

A dental primer includes: a (meth)acrylate having an acid group; a vanadium compound and/or a copper compound; a polymerization inhibitor; and water. In the dental primer, a content of the (meth)acrylate having the acid group is in a range of from 15% by mass to 60% by mass, a total content of the vanadium compound and the copper compound is in a range of from 0.25% by mass to 0.45% by mass, and a content of the polymerization inhibitor is in a range of from 0.8% by mass to 3% by mass.

7 Claims, No Drawings

DENTAL PRIMER AND KIT FOR DENTAL PROSTHESIS ADHESION

CROSS-REFERENCE TO RELATED APPLICATION

The present application is based upon and claims the benefit of priority of Japanese Patent Application No. 2017-067025, filed on Mar. 30, 2017, the entire contents of which are incorporated herein by reference.

BACKGROUND OF THE INVENTION

1. Field of the Invention

The present invention relates to a dental primer and a kit that is used for adhesion of a dental prosthesis.

2. Description of the Related Art

When dental cement is used to attach a dental prosthesis to a tooth surface, adhesiveness of the dental cement can be enhanced by applying in advance a dental primer to the tooth surface. At this time, the dental cement may be applied to the dental prosthesis other than being applied to the tooth surface.

By adding various constituents to a dental primer, adhesiveness of dental cement can be further enhanced.

Patent Document 1 discloses a dental primer that includes (meth)acrylate having an acid group, water, a water-soluble volatile organic solvent, and a vanadium compound.

However, it is desired to enhance preservation stability of a dental primer.

RELATED-ART DOCUMENTS

Patent Document

[Patent Document 1] Japanese Unexamined Patent Application Publication No. 2010-280630

SUMMARY OF THE INVENTION

Hence, one aspect of the present invention has an object to provide a dental primer that has an excellent preservation stability and is able to enhance adhesiveness of dental cement.

According to one aspect of the present invention, a dental primer includes: a (meth)acrylate having an acid group; a vanadium compound and/or a copper compound; a polymerization inhibitor; and water, wherein a content of the (meth)acrylate having the acid group is in a range of from 15% by mass to 60% by mass, wherein a total content of the vanadium compound and the copper compound is in a range of from 0.25% by mass to 0.45% by mass, and wherein a content of the polymerization inhibitor is in a range of from 0.8% by mass to 3% by mass.

According to one aspect of the present invention, it is possible to provide a dental primer that has an excellent preservation stability and is able to enhance adhesiveness of dental cement.

DESCRIPTION OF THE PREFERRED EMBODIMENTS

In the following, an embodiment of the present invention will be described.

<Dental Primer>

A dental primer according to the embodiment includes a (meth)acrylate having an acid group; a vanadium compound and/or a copper compound; a polymerization inhibitor; and water.

The dental primer according to the embodiment may further include an organic solvent, a (meth)acrylate not having an acid group, a filler, a reducing agent, and the like.

In the following, constituents that constitute the dental primer will be described.

<(Meth)acrylate Having an Acid Group>

In the specification and claims, a (meth)acrylate means various kinds of monomers, oligomers, and prepolymers of acrylate or methacrylate and includes one or more (meth)acryloyloxy groups. Further, the (meth)acryloyloxy group means a methacryloyloxy group or an acryloyloxy group.

The dental primer according to the embodiment includes a (meth)acrylate having an acid group. Therefore, it is possible to enhance the adhesiveness of dental cement.

Examples of the (meth)acrylate having an acid group include a (meth)acrylate having a phosphate group, a (meth)acrylate having a thiophosphate group, a (meth)acrylate having a carboxyl group, and the like. Two or more kinds of these may be used in combination as the (meth)acryloyloxy group having an acid group.

The (meth)acrylate having an acid group may include a plurality of acid groups.

Acidities of phosphate groups or thiophosphate groups are stronger than acidities of carboxyl groups. Hence, when the dental primer includes a (meth)acrylate having a phosphate group or a thiophosphate group, it is possible to improve solubility of a smear layer of a tooth surface and decalcification of dentine. Particularly, it is possible to enhance adhesiveness of dental cement to enamel.

Examples of the (meth)acrylate having a phosphate group include 2-(meth)acryloyloxyethyldihydrogen phosphate, bis[2-(meth)acryloyloxyethyl]hydrogen phosphate, 2-(meth)acryloyloxyethylphenylhydrogen phosphate, 6-(meth)acryloyloxyhexyldihydrogen phosphate, 6-(meth)acryloyloxyhexylphenylhydrogen phosphate, 10-(meth)acryloyloxydecyldihydrogen phosphate, 1,3-di(meth)acryloylpropane-2-dihydrogen phosphate, 1,3-di(meth)acryloylpropane-2-phenylhydrogen phosphate, bis[5-{2-(meth)acryloyloxyethoxycarbonyl}heptyl]hydrogen phosphate, and the like. In particular, 10-(meth)acryloyloxydecyldihydrogen phosphate is preferable in terms of the adhesiveness of dental cement used in combination with the dental primer and in terms of the stability of the (meth)acrylate itself.

Examples of the (meth)acrylate having a carboxyl group include 4-(meth)acryloxyethyltrimellitic acid, 4-(meth)acryloxyethyltrimellitic anhydride, 4-(meth)acryloxydecyltrimellitic acid, 4-(meth)acryloxydecyltrimellitic anhydride, 11-(meth)acryloyloxy-1,1-undecanedicarboxylic acid, 1,4-di(meth)acryloyloxypyromellitic acid, 2-(meth)acryloyloxyethylmaleic acid, 2-(meth)acryloyloxyethylphthalic acid, 2-(meth)acryloyloxyethylhexahydrophthalic acid, and the like. In particular, 4-(meth)acryloxyethyltrimellitic acid and 4-(meth)acryloxyethyltrimellitic anhydride are preferable in terms of the adhesiveness of dental cement used in combination with the dental primer.

Examples of the (meth)acrylate having a thiophosphate group include 2-(meth)acryloyloxyethyldihydrogen thiophosphate, 3-(meth)acryloyloxypropyldihydrogen thiophosphate, 4-(meth)acryloyloxybutyldihydrogen thiophosphate, 5-(meth)acryloyloxypentyldihydrogen thiophosphate, 6-(meth)acryloyloxyhexyldihydrogen thiophosphate, 7-(meth)acryloyloxyheptyldihydrogen thiophosphate, 8-(meth)acryloyloxyoctyldihydrogen thiophosphate, 9-(meth)acryloyloxynonyldihydrogen thiophosphate, 10-(meth)acryloyloxydecyldihydrogen thiophosphate, 11-(meth)acryloyloxyundecyldihydrogen thiophosphate, 12-(meth)acryloyloxydodecyldihydrogen thiophosphate, 13-(meth)acryloyloxytridecyldihydrogen thiophosphate, 14-(meth)acryloyloxytetradecyldihydrogen thiophosphate, 15-(meth)acryloyloxypentadecyldihydrogen thiophosphate, 16-(meth)acryloyloxyhexadecyldihydrogen thiophosphate, 17-(meth)acryloyloxyheptadecyldihydrogen thiophosphate, 18-(meth)acryloyloxyoctadecyldihydrogen thiophosphate, 19-(meth)acryloyloxynonadecyldihydrogen thiophosphate, 20-(meth)acryloyloxyicosyldihydrogen thiophosphate, and the like. In particular, 10-(meth)acryloyloxydecyldihydrogen thiophosphate is preferable in terms of the adhesiveness of dental cement used in combination with the dental primer and in terms of the stability of the (meth)acrylate itself.

A content of the (meth)acrylate, having an acid group, in the dental primer is in a range of from 15% by mass to 60% by mass, and is preferably in a range of from 15% by mass to 30% by mass. If the content of the (meth)acrylate, having an acid group, in the dental primer is less than 15% by mass, the preservation stability of the dental primer decreases. If the content of the (meth)acrylate, having an acid group, in the dental primer exceeds 60% by mass, the uniformity of the dental primer decreases.

<Vanadium Compound and/or Copper Compound>

A vanadium compound and/or a copper compound acts as a reducing agent or a photopolymerization accelerator.

The vanadium compound used in the embodiment is not particularly limited. Examples of the vanadium compound include vanadium(III) tris acetylacetonate (V(acac)$_3$), vanadyl acetylacetonate (VO(acac)$_2$), vanadyl stearate, vanadium(III) naphthenate, vanadium(III) benzoylacetonate, and the like. Two or more kinds of these may be used in combination. In particular, vanadyl acetylacetonate is preferable.

The copper compound used in the embodiment is not particularly limited. Examples of the copper compound include copper(II) acetylacetonate, copper(II) 4-cyclohexylbutyrate, copper(II) acetate, copper(II) oleate, copper(II) sulfate, copper(II) chloride, copper(II) gluconate, copper(II) oleate, copper(II) disodium ethylenediaminetetraacetate, copper(II) chloride, copper(II) nitrate, copper(II) acetate, copper(II) acrylate, copper(II) methacrylate, and the like. Two or more kinds of these may be used in combination. In particular, copper(II) gluconate is preferable.

A total content of the vanadium compound and the copper compound in the dental primer is in a range of from 0.25% by mass to 0.45% by mass, and is preferably in a range of from 0.3% by mass to 0.4% by mass. If the total content of the vanadium compound and the copper compound in the dental primer is less than 0.25% by mass, the adhesiveness of dental cement used in combination with the dental primer decreases. If the total content of the vanadium compound and the copper compound in the dental primer exceeds 0.45% by mass, the preservation stability of the dental primer decreases.

Note that because of including a vanadium compound and/or a copper compound acting as a reducing agent, it is preferable that the dental primer according to the embodiment does not include an oxidizing agent as a chemical polymerization initiator. Thereby, the preservation stability of the dental primer is enhanced.

<Polymerization Inhibitor>

The polymerization inhibitor used in the embodiment is not particularly limited. Examples of the polymerization inhibitor include dibutylhydroxytoluene, 2,6-t-butyl-2,4-xylenol, and the like. Two or more kinds of these may be used in combination.

A content of the polymerization inhibitor in the dental primer is in a range of from 0.8% by mass to 3% by mass, and is preferably in a range of from 1% by mass to 2% by mass. If the content of the polymerization inhibitor in the dental primer is less than 0.8% by mass, the preservation stability of the dental primer decreases. If the content of the polymerization inhibitor in the dental primer exceeds 3% by mass, the adhesiveness of dental cement used in combination with the dental primer decreases.

<Water>

Because the dental primer according to the embodiment includes water, the acid group of the (meth)acrylate having the acid group is dissociated, and the dental primer according to the embodiment acts as a self-etching primer. As a result, solubility of a smear layer of a tooth surface, decalcification of dentine, and permeability to dentine are enhanced. Therefore, the dental primer can be used without performing a pretreatment of a tooth surface with a phosphoric acid etching solution or the like. Further, when a pretreatment with a phosphoric acid etching solution or the like is performed on a tooth surface in advance, permeability to dentine is more enhanced, and the adhesiveness of dental cement used in combination with the dental primer is enhanced.

A content of water in the dental primer is preferably in a range of from 10% by mass to 50% by mass, and is more preferably in a range of from 20% by mass to 40% by mass. When the content of water in the dental primer is greater than or equal to 10% by mass, solubility of a smear layer of a tooth surface, decalcification of dentine, and permeability to dentine are enhanced. When the content of water in the dental primer is less than or equal to 50% by mass, the uniformity of the dental primer is enhanced.

<Organic Solvent>

The organic solvent used in the embodiment is not particularly limited. Examples of the organic solvent include methanol, ethanol, propanol, isopropanol, butanol, pentanol, acetone, methyl ethyl ketone, methyl isobutyl ketone, toluene, xylene, ethyl acetate, butyl acetate, cellosolve, tetrahydrofuran, dioxane, dichloromethane, chloroform, carbon tetrachloride, trichlorethylene, dimethylformamide, dimethylsulfoxide, and the like. Two or more kinds of these may be used in combination. Among these solvents, acetone and ethanol are particularly preferable.

A content of the organic solvent in the dental primer is preferably in a range of from 5% by mass to 70% by mass, and is more preferably in a range of from 10% by mass to 40% by mass. When the content of the organic solvent in the dental primer is greater than or equal to 10% by mass, the drying property of the dental primer is enhanced. When the content of the organic solvent in the dental primer is less than or equal to 40% by mass, the uniformity of the dental primer is enhanced.

<(Meth)Acrylate not Having an Acid Group>

The (meth)acrylate not having an acid group used in the embodiment is not particularly limited. Examples of the (meth)acrylate not having an acid group include methyl (meth)acrylate, ethyl (meth)acrylate, isopropyl (meth)acrylate, n-butyl (meth) acrylate, isobutyl (meth) acrylate, hydroxypropyl (meth) acrylate, tetrahydrofuryl (meth)acrylate, glycidyl (meth)acrylate, 2-hydroxyethyl (meth)acrylate, 2-hydroxypropyl (meth)acrylate, 3-hydroxypropyl (meth)acrylate, 2-methoxyethyl (meth) acrylate, 2-ethoxyethyl (meth)acrylate, 2-methylhexyl (meth)acrylate, 2-ethylhexyl (meth)acrylate, benzyl (meth)acrylate, 2-hydroxy-1,3-di(meth)acryloxy propane, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, pentaerythritol tri(meth)acrylate, trimethylolmethane tri(meth)acrylate, pentaerythritol tetra(meth)acrylate, polybutylene glycol di(meth)acrylate, bisphenol A glycidyl (meth)acrylate, and the like. Examples of the (meth)acrylate not having an acid group further include di-2-(meth)acryloxyethyl-2,2,4-trimethylhexamethylene dicarbamate, 1,3,5-tris[1,3-bis{(meth)acryloyloxy}-2-propoxycarbonylaminohexane]-1,3,5-(1H,3H,5H)triazine-2,4,6-trione, 2,2-bis-4-(3-(meth)acryloxy-2-hydroxypropyl)-phenylpropane, N,N'-(2,2,4-trimethylhexamethylene)bis[2-(aminocarboxy)propane-1,3-diol]tetramethacrylate, a (meth)acrylate of an urethane oligomer including 2,2'-di(4-hydroxycyclohexyl) propane, 2-oxypanone, hexamethylene diisocyanate, and 2-hydroxyethyl (meth)acrylate, a (meth)acrylate of an urethane oligomer including 1,3-butanediol, hexamethylene diisocyanate, and 2-hydroxyethyl (meth)acrylate, and the like. In particular, 2-hydroxy-1,3-di(meth)acryloxy propane is preferable.

A content of the (meth)acrylate, not having an acid group, in the dental primer is preferably in a range of from 0.5% by mass to 45% by mass, and is more preferably in a range of from 10% by mass to 35% by mass. When the content of the (meth)acrylate, not having an acid group, in the dental primer is greater than or equal to 0.5% by mass, the adhesiveness of dental cement used in combination with the dental primer is enhanced. When the content of the (meth) acrylate, not having an acid group, in the dental primer is less than or equal to 45% by mass, contents of other constituents can be secured and the preservation stability of the dental primer is enhanced.

<Filler>

A filler used in the embodiment may be either an organic filler or an inorganic filler, and is preferably an inorganic filler.

The inorganic filler used in the embodiment is not particularly limited. Examples of the inorganic filler include silica powder, fumed silica, alumina powder, glass powder (for example, barium glass powder or fluoroaluminosilicate glass powder), and the like. Two or more kinds these may be used in combination.

The inorganic filler may be processed by a surface treatment agent such as a silane coupling agent as needed.

A content of the filler in the dental primer is preferably in a range of from 0.1% by mass to 20% by mass, and is more preferably in a range of from 0.5% by mass to 10% by mass. When the content of the filler in the dental primer is greater than or equal to 0.1% by mass and less than or equal to 20% by mass, the adhesiveness of dental cement used in combination with the dental primer is enhanced.

<Reducing Agent>

A reducing agent used in the embodiment is not particularly limited. Examples of the reducing agent include amine compounds, sulfinic acids, thioureas, cysteines, ascorbic acids, and the like. Two or more kinds of these may be used in combination.

Examples of the amine compounds include N,N-dimethyl-p-toluidine, N,N-diethyl-p-toluidine, N,N-dimethyl-aniline, N,N-bis(2-hydroxyethyl)-p-toluidine, N,N-dimethylaminoethyl methacrylate, triethanolamine, methyl 4-dimethylaminobenzoate, ethyl 4-dimethylaminobenzoate, isoamyl 4-dimethylaminobenzoate, triethylamine, N-ethyl-diethanolamine, triethanolamine, N-phenylglycine, and the like.

Examples of the sulfinic acids include sodium p-toluenesulfinate, lithium p-toluenesulfinate, benzenesulfinic acid, sodium benzenesulfinate, p-toluenesulfonyl chloride, p-toluenesulfonyl fluoride, o-toluenesulfonyl isocyanate, sodium p-acetamidobenzenesulfinate, and the like.

Examples of the thioureas include thiourea, ethylene thiourea, N-methylthiourea, N-ethylthiourea, N-propylthiourea, N-butylthiourea, N-laurylthiourea, N-phenylthiourea, N-cyclohexylthiourea, N,N-dimethylthiourea, N,N-diethylthiourea, N,N-dipropylthiourea, N,N-di-butylthiourea, N,N-dilaurylthiourea, N,N-diphenylthiourea, N,N-dicyclohexylthiourea, trimethylthiourea, tetramethylthiourea, N-acetylthiourea, N-benzoylthiourea, 1-allyl-3-(2-hydroxyethyl)-2-thiourea, 1-(2-tetrahydrofurfuryl)-2-thiourea, and the like. In particular, N-benzoylthiourea is preferable.

Examples of the cysteines include derivatives of cysteine and derivatives of cysteine.

Examples of the derivatives of cysteine include cysteine methyl, cysteine ethyl, N-methylcysteine, N-ethylcysteine, N-acetylcysteine, N,N-dimethylcysteine, N,N-diethylcysteine, N,N-diacetylcysteine, glutathione, and the like.

Examples of the ascorbic acids include ascorbic acid, sodium ascorbate, calcium ascorbate, potassium ascorbate, and the like.

A content of the reducing agent in the dental primer is preferably in a range of from 0.1% by mass to 10% by mass, and is more preferably in a range of from 0.2% by mass to 5% by mass. When the content of the reducing agent in the dental primer is greater than or equal to 0.1% by mass and less than or equal to 10% by mass, the adhesiveness of dental cement used in combination with the dental primer is enhanced.

<Kit for Dental Prosthesis Adhesion>

A dental primer according to the embodiment may be used in combination with dental cement that includes an oxidizing agent such that a dental prosthesis can adhere to a tooth surface (for example, see Patent Document 1). The dental cement may further include a photopolymerization initiator as needed. In other words, a kit that, which is used for adhesion of a dental prosthesis, may include a dental primer according to the embodiment as described above; and dental cement including an oxidizing agent.

Note that the dental cement may be a self-adhesive resin cement that includes a (meth)acrylate having an acid group, or may be a resin cement, used in combination with a primer, that does not include a (meth)acrylate having an acid group.

Examples of a material constituting the dental prosthesis include a resin such as a composite resin, an alloy including a precious metal, ceramics such as zirconia and alumina, and the like.

WORKING EXAMPLES

In the following, the present invention will be described in more details with reference to specific working examples and comparative examples. The present invention is not limited to these working examples.

Working Examples 1 to 10 and Comparative Examples 1 to 7

At a composition [% by mass] illustrated in the table 1, the organic solvent, water, the polymerization inhibitor, the (meth)acrylate having an acid group, the (meth)acrylate not having an acid group, the vanadium compound, the copper compound, the reducing agent, the filler were mixed to prepare a primer for each of the working examples and the comparative examples.

Note that the abbreviated names used in the table 1 mean as follows.

BHT: dibutylhydroxytoluene
IA: 2,6-t-butyl-2,4-xylenol
MDTP: 10-methacryloyloxydecyldihydrogen thiophosphate
4-MET: 4-methacryloyloxyethyl trimellitic anhydride
MDP: 10-methacryloyloxydecyldihydrogen phosphate
GDMA: 2-hydroxy-1,3-dimethacryloyloxypropane
VAA: vanadyl acetylacetonate
$Cu(Glu)_2$: copper(II) gluconate
NBTU: N-benzoylthiourea
alumina powder: AEROXIDE (registered trademark) AluC (manufactured by NIPPON AEROSIL CO., LTD)
silica powder: AEROSIL (registered trademark) R812 (manufactured by NIPPON AEROSIL CO., LTD)

Next, the preservation stability of the primer and the adhesiveness of resin cement, when used in combination with the primer, to dentine were evaluated for each of the working examples and the comparative examples.

<Preservation Stability>

After the primer was sealed in a container made of high density polyethylene and left for two weeks under an environment of 60° C., the state of the primer was visually checked to evaluate the preservation stability of the primer for each of the working examples and the comparative examples. Note that the determination criteria for the preservation stability are as follows.

Good: neither gelation nor discoloration of the primer was identified

Poor: either gelation or discoloration of the primer was identified

<Adhesiveness to Dentine of Resin Cement when Used in Combination with the Primer>

After a stainless steel rod having a diameter of 10 mm was polished by #120 water-resistant abrasive paper, a sandblasting process was performed to obtain a jig for tensile test.

Dentine of a bovine tooth was polished by #320 water-resistant abrasive paper. To the flat polished surface, a polytetrafluoroethylene seal, having a hole of which diameter is 2.5 mm and having a thickness of 100 μm, was attached to define an area of the adhered surface.

The primer was applied to the adhered surface of the dentine of the bovine tooth. After leaving it 10 seconds, it was dried by blown air.

After an appropriate amount of a kneaded substance of G-CEM CERASMART (manufactured by GC Corporation) as a self-adhesive resin cement was applied to the rod, it was pressed to contact the adhered surface of the dentine of the bovine tooth. Next, the redundant cement was removed by a probe. After leaving it one hour under an environment of 37° C. and 95% RH, it was immersed into distilled water of 37° C. 23 hours to obtain a test object.

A precise universal tester autograph AG-1 (manufactured by Shimadzu Corporation) was used under conditions of a crosshead speed of 1 mm/minute to conduct a tensile test for five test objects. Then, an average value of tensile bond strength was obtained to evaluate the adhesiveness of resin cement to dentine when used in combination with the primer, for each of the working examples and the comparative examples. Note that the determination criteria for the adhesiveness of resin cement, when used in combination with the primer, to dentine were as follows.

Very good: the average value of tensile bond strength was greater than or equal to 15 MPa Good: the average value of tensile bond strength was greater than or equal to 10 MPa and less than 15 MPa Fair: the average value of tensile bond strength was greater than or equal to 6 MPa and less than 10 MPa Poor: the average value of tensile bond strength was less than 6 MPa The table 1 indicates the preservation stability of the primer and the adhesiveness of resin cement to dentine, when used in combination with the primer, for each of the working examples and the comparative examples.

TABLE 1

|  |  | WORKING EXAMPLE | | | | | | | | | |
|---|---|---|---|---|---|---|---|---|---|---|---|
|  |  | 1 | 2 | 3 | 4 | 5 | 6 | 7 | 8 | 9 | 10 |
| ORGANIC SOLVENT | ETHANOL | 39.7 | 38.7 |  | 26.7 | 39.7 | 38.1 | 39.6 | 27.45 | 37.0 | 31.7 |
|  | ACETONE |  |  | 37.6 |  |  |  |  |  |  |  |
| WATER | DISTILLED WATER | 25 | 25 | 25 | 35 | 25 | 25 | 21 | 25 | 25 | 25 |
| POLYMERIZATION INHIBITOR | BHT | 1 | 1 | 2 | 1 | 1 | 1.5 | 0.8 | 2 | 1.5 | 1 |
|  | IA |  |  |  |  |  |  | 1 |  |  | 0.8 |
| (METH)ACRYLATE HAVING ACID GROUP | MDTP |  |  |  |  |  | 0.1 | 0.3 | 0.1 | 0.2 | 0.1 |
|  | 4-MET | 10 |  | 10 | 15 | 24 | 5 | 10 | 15 | 8 | 10 |
|  | MDP | 9 | 20 | 15 | 12 |  | 10 | 10 | 15 | 16 | 9 |
| (METH)ACRYLATE NOT HAVING ACID GROUP | GDMA | 15 | 15 | 10 | 10 | 10 | 20 | 15 | 10 | 10 | 15 |
| VANADIUM COMPOUND | VAA | 0.3 | 0.3 | 0.4 | 0.3 |  | 0.35 | 0.3 | 0.4 |  |  |
| COPPER COMPOUND | $Cu(Glu)_2$ |  |  |  |  | 0.3 |  |  |  | 0.3 | 0.35 |
| REDUCING AGENT | NBTU |  |  |  |  |  |  |  | 2 | 2 | 2 |
| FILLER | ALUMINA POWDER |  |  |  |  |  |  |  | 0.35 |  | 0.35 |
|  | SILICA POWDER |  |  |  |  |  |  |  | 4.7 |  | 4.7 |
| TOTAL |  | 100 | 100 | 100 | 100 | 100 | 100 | 100 | 100 | 100 | 100 |

TABLE 1-continued

| | | | | | | | | | | |
|---|---|---|---|---|---|---|---|---|---|---|
| PRESERVATION STABILITY | | GOOD | GOOD | GOOD | GOOD | GOOD | GOOD | GOOD | GOOD | GOOD | GOOD |
| ADHESIVENESS | | VERY GOOD | GOOD | VERY GOOD | VERY GOOD | GOOD | VERY GOOD | VERY GOOD | VERY GOOD | VERY GOOD | VERY GOOD |

| | | | COMPARATIVE EXAMPLE | | | | | | |
|---|---|---|---|---|---|---|---|---|---|
| | | | 1 | 2 | 3 | 4 | 5 | 6 | 7 |
| ORGANIC SOLVENT | ETHANOL ACETONE | | 51.7 | 39.5 | 40.2 | 35.7 | 39.85 | 53.7 | 47.6 |
| WATER | DISTILLED WATER | | 25 | 25 | 25 | 25 | 25 | 25 | 25 |
| POLYMERIZATION INHIBITOR | BHT IA | | 1 | 1 | 0.5 | 5 | 1 | 1 | 1 |
| (METH)ACRYLATE HAVING ACID GROUP | MDTP 4-MET MDP | | 3 4 | 10 9 | 10 9 | 10 9 | 10 9 | 5 | 0.1 11 |
| (METH)ACRYLATE NOT HAVING ACID GROUP | GDMA | | 15 | 15 | 15 | 15 | 15 | 15 | 15 |
| VANADIUM COMPOUND | VAA | | 0.3 | 0.5 | 0.3 | 0.3 | 0.15 | 0.3 | 0.3 |
| COPPER COMPOUND | Cu(Glu)$_2$ | | | | | | | | |
| REDUCING AGENT | NBTU | | | | | | | | |
| FILLER | ALUMINA POWDER SILICA POWDER | | | | | | | | |
| TOTAL | | | 100 | 100 | 100 | 100 | 100 | 100 | 100 |
| PRESERVATION STABILITY | | | POOR | POOR | POOR | GOOD | GOOD | POOR | POOR |
| ADHESIVENESS | | | FAIR | VERY GOOD | VERY GOOD | POOR | POOR | POOR | FAIR |

It is found, from the table 1, that the primers of the working examples 1 to 10 had high preservation stability. Further, when the primers of the working examples 1 to 10 were used in combination, the adhesiveness of resin cement to dentine became high.

On the other hand, in the comparative examples 1, 6, and 7, because the content of the (meth)acrylate having an acid group was in a range of from 5% by mass to 11.1% by mass, the preservation stability was low.

In the primer of the comparative example 2, because the content of the vanadium compound was 0.5% by mass, the preservation stability was low.

In the primer of the comparative example 3, because the content of the polymerization inhibitor was 0.5% by mass, the preservation stability was low.

In the primer of the comparative example 4, the content of the polymerization inhibitor was 5% by mass. Hence, when the primer of the comparative example 4 was used in combination, the adhesiveness of resin cement to dentine became low.

In the primer of the comparative example 5, the content of the vanadium compound was 0.15% by mass. Hence, when the primer of the comparative example 5 was used in combination, the adhesiveness of resin cement to dentine became low.

What is claimed is:

1. A one-part dental primer comprising:
   a (meth)acrylate having an acid group;
   a vanadium compound and/or a copper compound;
   a polymerization inhibitor;
   an organic solvent containing ethanol; and
   water,
   wherein a content of the (meth)acrylate having the acid group is in a range of from 15% by mass to 60% by mass,
   wherein a total content of the vanadium compound and the copper compound is in a range of from 0.25% by mass to 0.45% by mass,
   wherein a content of the polymerization inhibitor is in a range of from 0.8% by mass to 3% by mass,
   wherein a content of the organic solvent is in a range of from 10% by mass to 40% by mass, and
   wherein the dental primer does not include a polymerizable monomer having a fluorocarbon group.

2. A kit that is used for adhesion of a dental prosthesis, the kit comprising
   the one-part dental primer according to claim 1; and
   dental cement including an oxidizing agent.

3. The one-part dental primer according to claim 1, further comprising:
   a (meth)acrylate not having an acid group,
   wherein the (meth)acrylate not having an acid group is a polyfunctional (meth)acrylate.

4. The one-part dental primer according to claim 3, wherein a content of the (meth)acrylate not having an acid group is in a range of from 0.5% by mass to 45% by mass.

5. The one-part dental primer according to claim 1, wherein the content of the water is less than or equal to 50% by mass.

6. The one-part dental primer according to claim 1, wherein the (meth)acrylate includes a (meth)acrylate having a thiophosphate group.

7. The one-part dental primer according to claim 1, wherein the content of the water is greater than or equal to 25% by mass.

* * * * *